United States Patent [19]

Rebeiz

[11] 3,934,369
[45] Jan. 27, 1976

[54] VITRO NET BIOXYNTHESIS OF CHLOROPHYLL AND GRANA

[75] Inventor: Constantin Anis Rebeiz, Champaign, Ill.

[73] Assignee: University of Illinois Foundation, Urbana, Ill.

[22] Filed: Apr. 23, 1974

[21] Appl. No.: 463,353

[52] U.S. Cl. .................................. 47/58; 195/1
[51] Int. Cl.² ................................... A01G 1/00
[58] Field of Search .................. 47/1, 58; 195/1

[56] References Cited
OTHER PUBLICATIONS

Hatch et al., Photosynthesis and Photorespiration, Wiley–Interscience, New York, 1971.

Primary Examiner—Alvin E. Tanenholtz
Attorney, Agent, or Firm—Merriam, Marshall, Shapiro & Klose

[57] ABSTRACT

In vitro net biosynthesis of chlorophyll and grana involving: irradiation of etiolated plant tissue; homogenization, in an environment including available oxygen, of the tissue in a buffer comprising biosynthetic cofactors including coenzyme A, glutathione, potassium, inorganic phosphate, methyl alcohol, magnesium, nicotinamide adenine dinucleotide and adenosine triphosphate; isolation from the homogenate of developing chloroplasts; irradiated incubation of the isolated chloroplasts in the presence of oxygen in another buffer of a constitution similar to that above-described and including δ aminolevulinic acid. Synthesized products are isolated and quantified.

17 Claims, 6 Drawing Figures

IN VITRO NET BIOXYNTHESIS OF CHLOROPHYLL AND GRANA

BACKGROUND

The present invention relates generally to in vitro biosynthetic systems and products thereof and more specifically to the net biosynthesis, in vitro, of chlorophyll and grana.

The prime source of energy in the biosphere is the light absorbed by chlorophyll-containing plant cells. This energy is used to fix carbon dioxide into carbohydrates by the following general formula.

$$6\ CO_2 + 6\ H_2O \xrightarrow{light} C_6H_{12}O_6 + 6\ O_2$$

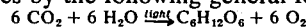

The photosynthetic apparatus of plant and algal cells is lodged within especially organized structures called chloroplasts, which are bodies of varied shape, 3 to 10 $\mu$ long and 0.5 to 2 $\mu$ in diameter. Within chloroplasts are found varying numbers of somewhat cylindrical structures called grana, which generally include fused stacks of flattened membranes called thylakoids. At or near the thylakoid membranes in grana, substantial portions of the photosynthetic process occur.

Extensive research into the process of biosynthesis of chlorophyll in lower and higher plants has been carried out, reported and reviewed within the past two decades. See, e.g., the references collected and cited by the inventor in, Rebeiz, et al., *Ann. Rev. Plant. Physiol.*, 24, 129–72 at p. 131. The step-by-step enzymology of chlorophyll biosynthesis is still not completely known. The middle portion of the biosynthetic pathway, i.e., the stepwise conversion of δ-aminolevulinic acid (hereafter, ALA) to protoporphyrin IX, has been explored with moderate success in cell-free preparations from higher plants. However, the initial step involving ALA biosynthesis and the final steps involving conversion of protoporphyrin to chlorophyll are still largely unknown. Progress in these two areas has been held back by the lack of cell-free, in vitro, systems able to catalyze these reactions. The lack of such systems has been in major part due to the general inability to suppress in vitro, the "auto-destructive" activity of chloroplasts and related organelles upon their removal from in vivo systems.

In the last decade considerable efforts have been devoted to evaluating the reproductive, developmental and nutritional autonomy of chloroplasts. The control of chlorophyll biosynthesis and biosynthesis of thylakoid membranes have also received considerable attention. See, e.g., the reviews dealing with this topic collected and cited by the inventor in Rebeiz, et al., supra, at p. 132. Here, too, the progress of the field has been hindered by the lack of chloroplast preparations capable of doing in vitro, what they can be in vivo (see, e.g., Woodcock, et al., in "Structure and Function of Chloroplasts," (ed., Gibbs), pp. 89–128 (New York: Springer-Verlag, 1971)).

The inventor and his collaborators have shown that cell-free homogenates and etioplasts isolated from cucumber cotyledons and incubated with $^{14}$C-ALA and certain biosynthetic cofactors are capable of synthesizing $^{14}$C-Mg protoporphyrin monoester, $^{14}$C-Protochlorophyll and $^{14}$C-chlorophyll a and b. See, Rebeiz, et al., *Plant Physiol.*, 47, 24–32 (1971); Rebeiz, et al., *Plant Physiol.*, 47, 33–37 (1971); and Rebeiz, et al., *Plant Physiol.*, 46, 543–49 (1970). Confirmation of that work was reported by Wellburn, et al., in *Biochem. and Biophys, Res. Comm.*, 45, 747–50 (1971). (See also, Wellburn, et al., *J. Experimental. Bot.*, 22, 972–79 (1971) and Wellburn, et al., *J. Cell. Sci.*, 9, 271–87 (1971).)

The net biosynthesis of microgram quantities of chlorophyll from ALA in vitro has, however, heretofore not been achieved. Similarly, the biosynthetic in vitro assembly of grana has heretofore not been achieved.

BRIEF DESCRIPTION

According to the present invention the in vitro net biosynthesis of chlorophyll as well as the in vitro biosynthesis of grana may be achieved through processes involving the irradiation of etiolated plant tissue with visible light (i.e., 350 to 1,050 nm) at an intensity of 100 to 300 foot-candles for periods of 2 to 5 hours at temperatures of from 20° to 35°C. to precipitate the formation of developing chloroplasts. The irradiation process is followed by an homogenization of the irradiated tissue in an atmosphere containing available oxygen (such as air) and in a buffer comprising biosynthetic cofactors including coenzyme A (hereafter, CoA), glutathione (hereafter, GSH), potassium, inorganic phosphate (hereafter, Pi), methyl alcohol, magnesium, nicotinamide adenine dinucleotide (hereafter, NAD) and adenosine triphosphate (hereafter, ATP) which buffer has a pH of 7.9 to 8.2, as measured at an ambient temperature of about 20°C. The homogenization process is followed by isolation of developing chloroplasts from the homogenate and subsequent incubation, while irradiating with visible light at an intensity of 1 to 50 foot-candles and in an atmosphere containing available oxygen, in a buffer of a constitution similar to that above-described, but which includes ALA and has a pH of 7.6 to 7.8, as measured at an ambient temperature of about 20°C. The incubation is ordinarily carried out at temperatures of 15° to 35°C. Chlorophyll and grana formed in the course of the incubation may be isolated and characterized.

As employed herein, "chlorophyll" relates to the green coloring material visible in leaves and present in all growing plants and includes chlorophyll a and b, unless otherwise indicated or made obvious from the context. The term "grana" relates to contiguously fused membranous material ordinarily characterized by the presence of chlorophyll, cytochromes, galactolipids, digalactolipids, sulpholipids, plastoquinones, carotenoids, phospholipids, diphospholipids, plastocyanin, ferredoxin and other lipid and proteinaceous materials (See, e.g., the molecular models of such membranous materials described by Weier, et al., in "The Biochemistry of Chloroplasts," (ed., Goodwin) pp. 92–113 (London: Academic Press, 1966).) The exact chemical and physical nature of grana membranous fusion is incompletely known, but it is expected that the fusion may include bonding by van der Waals forces, hydrogen bonding, ionic bonding, hydrophobic association and, possibly, covalent bonding. The term "net biosynthesis" relates to a detectable measurable increase in the net amount of a particular product synthesized during a given period of time. A measurable increase, relative to an in vitro biosynthetic system, for example, might ordinarily be such an amount as may be weighed in microgram quantities. The term "etiolated plant tissue" relates to plant tissue grown in the absence of light and which contains some amount of prolamellar bodies and protochlorophyll, but which contains neither grana nor substantial amounts of chlorophyll. (It may be noted, for example, that etiolated pine seedling tissue has been reported to contain minor amounts of chlorophyll.)

As indicated supra, the processes of the present invention may be carried out within a moderately wide range of process parameters. Preferred parameters will become apparent through consideration of the following detailed description of processes and products, reference being made to the drawings wherein:

FIG. 1 graphically represents apparent fluorescence of precipitated and suspended chlorophyll-protein pellets;

FIG. 2 graphically represents absorption and difference spectra of organic extracts of developing chloroplasts;

FIG. 3 graphically represents apparent fluorescence of various bound chlorophyll fractions;

Figure 1:
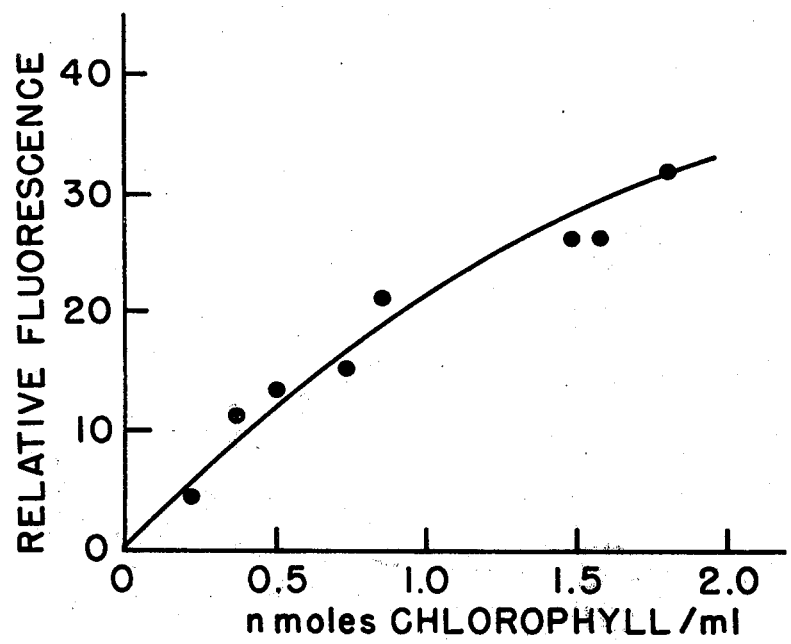

The processes and products of the present invention set out in the detailed description which follows are substantially as described by the inventor in: Rebeiz, et al., "Chloroplast Maintenance and Partial Differentiation in Vitro," *Plant Physiol.*, 51, 651–59 (1973); Rebeiz, et al., "Biosynthesis and Accumulation of Microgram Quantities of Chlorophyll by Developing Chloroplasts in Vitro," *Plant Physiol.*, 51, 660–66 (1973) and Rebeiz, et al., "Protochlorophyll and Chlorophyll Biosynthesis in Cell-Free Systems from Higher Plants," *Ann. Rev. Plant Physiol.*, 24, 129–72 (1973). The disclosure of these publications as it relates to the background of the invention and illustrates the prior art is hereby expressly incorporated by reference.

DETAILED DESCRIPTION

The in vitro biosynthesis of grana according to the present invention may be illustrated by the following exemplary procedures, generally designated as "Procedure I."

PROCEDURE I

A. Materials and Methods

1. Growing, Harvesting, and Irradiating Cucumber Cotyledons

Cucumber seeds, (*Cucumis sativus* L. cv. Alpha Green) were germinated in vermiculite at 24°C. in complete darkness for 4.5 days. Cotyledons to be preirradiated were harvested with full hypocotyl hook. (See, Hardy, et al., *Plant Physiol.*, 46, 705–07 (1970).) They were placed in beakers with enough distilled water to keep them moist and were illuminated with 240 foot-candles of white fluorescent light at 28°C. for 2.5 or 4.5 hours.

2. Preparation of Unfortified and Fortified Crude Homogenates

"Unfortified" crude homogenates were prepared from 4.5-day-old cotyledons as follows. Four grams of etiolated or greening cotyledons were gently ground with mortar and pestle without sand in 6.0 ml. of 0.5 molar (hereafter, M) sucrose and 0.2 M tris-HCl, pH 8.0, at 0° to 5°C. The brei was filtered through four layers of cheesecloth. About 5 ml. of unfortified crude homogenates were obtained. "Fortified" crude homogenates were prepared by grinding 4 g. of etiolated or greening cotyledons in 6.0 ml. of fortified tris-HCl and 0.5 M sucrose, pH 8.0, containing 5 $\mu$moles of GSH, 0.3 $\mu$mole of CoA, 0.5 $\mu$mole of magnesium chloride as a source of magnesium, 50 $\mu$mole of potassium phosphate as a source of both potassium and Pi, 24 $\mu$moles of methanol, 0.4 $\mu$mole of ATP, and 0.075 $\mu$mole of NAD per ml. of fortified buffer. The brei was filtered as described above. About 5 ml. of fortified crude homogenates were obtained.

3. Preparation of Etioplasts and Developing Chloroplasts

"Fortified" and "unfortified" etioplasts or developing chloroplasts refer to isolated organelle preparations obtained from the respective fortified or unfortified crude homogenates. Five ml. of the fortified or unfortified crude homogenates were centrifuged at 200 × g for 3 minutes. The pellet was discarded, and the supernatant was centrifuged at 1,500 × g for 7 minutes. The pellet obtained from the unfortified crude homogenate was resuspended in 4 ml. of 0.5 M sucrose and 0.2 M tris-HCl, pH 7.7 Such suspensions are referred to as unfortified etioplasts or unforitifed developing chloroplasts, as the case may be. The pellet obtained from a fortified crude homogenate was resuspended in 4 ml. of fortified 0.2 M tris-HCl and 0.5 M sucrose, pH 7.7, containing 5 $\mu$moles of GSH, 0.3 $\mu$mole of CoA, 0.5 $\mu$mole of magnesium chloride, 50 $\mu$moles of potassium phosphate, 24 $\mu$moles of methanol, 0.4 $\mu$mole of ATP, and 0.075 $\mu$mole of NAD per ml. of fortified buffer. Such plastid suspensions are referred to as fortified etioplasts or fortified developing chloroplasts. All manipulations involving etiolated preparations were performed in the dark under a weak green safelight. Preparations derived from greening cotyledons were handled under subdued laboratory light, including natural sunlight and fluorescent artificial light, of about 10 foot-candles at bench level.

4. Incubation

Four ml. of unfortified and fortified crude homogenates, unfortified and fortified etioplasts, and unfortified and fortified developing chloroplasts were incubated in cylindrical flat bottom glass tubes (2 × 10 cm.) on a metabolic shaker operated at about 10 to 50 shakes/minute. The incubations were performed at 28°C., either in complete darkness or under 10 foot-candles of white fluorescent light for 16 hours. Reaction mixtures that were incubated in the absence of light were wrapped in black cloth and covered with aluminum foil, and the incubation was carried out in a darkroom. The unfortified reaction mixture (5.0 ml.) at pH 7.7 contained 4.0 ml. of unfortified crude homogenates or unfortified plastid preparations, 800 $\mu$moles of tris-HCl, 2 $\mu$moles of sucrose, and 120 nmoles of ALA. Five ml. of fortified reaction mixture at pH 7.7 contained 4.0 ml. of fortified crude homogenates or fortified plastid preparations, 800 $\mu$moles of tris-HCl, 2 mmoles of sucrose, 120 nmoles of ALA, 200 $\mu$moles of potassium phosphate, 2 $\mu$moles of magnesium chloride, 20 $\mu$moles of GSH, 1.2 $\mu$moles of CoA, 2.4 mmoles of methyl alcohol, 1.6 $\mu$moles of ATP, and 0.3 $\mu$mole of NAD. Preirradiated cotyledons excised with full hypocotyl hook were simultaneously incubated in a minimal volume of distilled water under the same light and temperature conditions.

5. Recovery of Incubated Plastids from Unfortified and Fortified Reaction Mixtures Containing Crude Homogenates At the beginning or end of incubation, unfortified or fortified reaction mixtures containing crude homogenates were centrifuged at 200 × g for 3 minutes to sediment debris. The pellet was discarded. The resulting supernatant was centrifuged at 1,500 × g for 7 minutes to sediment the plastids.

6. Recovery of Incubated Plastids from Unfortified and Fortified Reaction Mixtures Containing Isolated Plastid Preparations At the beginning or end of incubation the unfortified or fortified reaction mixtures containing etioplasts or developing chloroplasts were centrifuged at 1,500 × g for 7 minutes to sediment the plastids.

7. Electron Microscopic Study

The plastid pellets were suspended in 1 ml. of their respective incubation medium, and equal volumes of 4% glutaraldehyde were added. The suspensions were kept in the dark at room temperature for 45 minutes, then centrifuged at 1,500 × g for 10 minutes.

Pieces of cotyledons were fixed with 5% glutaraldehyde in 0.15 M phosphate buffer at pH 7.2 for 1 hour and were washed thoroughly in buffer. Both cotyledons and plastid pellets were postfixed in 1% osmium tetraoxide in 0.15 M phosphate buffer, pH 7.2. Dehydration was by an ethanol-propylene oxide series followed by embedding in a low viscosity epoxy resin according to Spurr, *J. Ultrastruct. Res.*, 26, 31–43 (1969). Sections were cut with a diamond knife in a microtrome and stained with a 2% aqueous uranyl acetate solution followed by lead citrate according to Reynolds, *J. Cell. Biol.*, 18, 208–12 (1963). Sections were examined in an electron microscope. Three grids were prepared from each pellet. Examination on the microscope preceded any evaluation of the final prints which were prepared by a technician without knowledge of the profile types desired. The only selection consisted of photographing etioplasts from each grid that showed some structure. Two hundred etioplasts from each grid were reviewed.

B. Results

1. General Ultrastructure of Etioplasts

Electron microscopic study of an unfortified crude homogenate containing etioplasts at zero time revealed the presence of intact and damaged etioplasts, prolamellar body debris, and mitochondria as well as other particulate components. The fixation image of the stroma of typical etioplasts found in this unfortified crude homogenate was uniformly finely gray-granular with some black granules and irregular areas free from electron-dense material. The prolamellar body was in the crystalline phase and had several peripheral lamellae radiating from it. There were occasional membrane overlaps in the peripheral lamellae.

After 16 hours of dark incubation in the adsence of cofactors the unfortified crude homogenate appeared severely bleached. Etioplasts could not be positively identified, although electron-dense homogeneous profiles with heavy osmiophilic centers which were revealed may represent etioplasts with strongly degraded prolamellar bodies. These profiles indicated a complete loss of the structured molecular organization of the etioplasts. Typical etioplasts were not observed after 16 hours of incubation in the dark in the fortified crude homogenate containing cofactors. However, some degraded etioplasts were tentatively identified as such. Many reticular profiles were present, some sectors of which were associated with a double membrane that could be interpreted as a plastid envelope. Thus, although the cofactors did not fully protect the etioplasts in the crude homogenate during the 16-hour dark incubation period, they seemed to retard the rate of breakdown.

Unfortified etioplasts incubated in the dark for 16 hours in the absence of cofactors lost much of their structural organization. For example, all the plastids in a representative sample of 15 profiles were highly degraded. In most cases there remained only a vesicular stroma which generally lacked an outer envelope. There was present in some etioplasts a limiting outer boundary that could be interpreted as a partially degraded outer envelope. No lamellar structures were observed.

Fortified etioplasts incubated in the dark for 16 hours in the presence of cofactors retained much of their structure. In a representative sample of 15 profiles, 5 etioplasts exhibited a distinct prolamellar body, including peripheral lamellae surrounded by a granular, moderately reticulate stroma. Such prolamellar bodies were not crystalline as might be expected since no irradiation was received, but rather resembled reacted prolemellar bodies, that is, ones that have lost their paracrystalline structure. Reacted prolamellar bodies are normally observed in etioplasts from seedlings that have received a short exposure to light. The envelope, while present, only infrequently showed its double nature. The remaining 10 profiles lacking prolamellar bodies were membrane-bound organelles. They were interpreted as sections of regions to one side of the prolamellar body. No irregular reticulate profiles were observed such as in unfortified etioplasts incubated without cofactors. The cofactors clearly protect the etioplasts in free suspension from degradation in the dark.

2. Ultrastructural Changes of Developing Chloroplasts Prepared from 2.5-hour-preilluminated Cotyledons and Incubated in the Light in the Absence and Presence of Cofactors.

Figure 4:
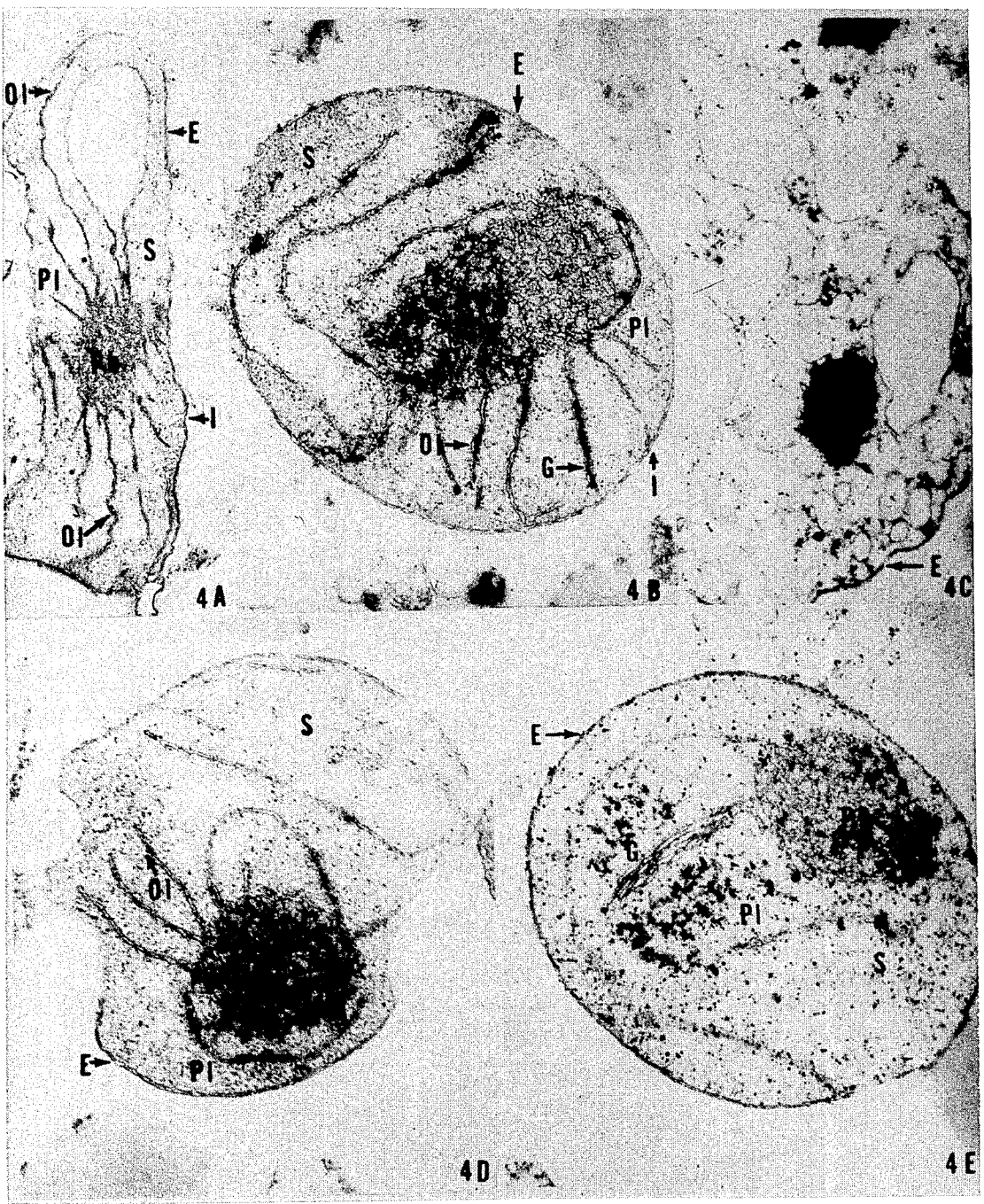
FIG. 4 is a composite comparative photomicrograph of developing chloroplasts.

FIG. 4 is a composite photomicrograph illustrating ultrastructural changes in developing chloroplasts obtained according to the invention through irradiation for 2.5 hours. Within the micrograph the following abbreviations are employed: E for envelope; G for granum; I for invagination and/or interaction of inner component of envelope with peripheral lamellae; Ol for overlapping of membranes in peripheral lamellae; Pb for prolamellar body, crystalline or reacted state; Pl for peripheral lamellae; S for stroma; and St for starch. FIG. 4A shows an in situ plastid from irradiated cotyledons; FIG. 4B shows an unfortified plastid at zero time; FIG. 4C shows an unfortified plastid after 16 hours of incubation without cofactors; FIG. 4D shows a fortified plastid at zero time; and FIG. 4E shows a foritifed plastid after 16 hours of incubation with cofactors. All micrographs are at a magnification of 18,000 ×.

Greening cucumber cotyledons irradiated for 2.5 hours contained etioplasts with a reacted prolamellar body and incipient two-compartment grana (FIG. 4A) associated with the peripheral lamellae. The plastids in a representative sample of 18 profiles were very similar to the one shown in FIG. 4A. The usual picture suggesting membrane proliferation from the inner component of the plastid envelope is also well illustrated. These cotyledons had just emerged from the lag phase.

FIGS. 4B and 4D, respectively, show unfortified and fortified plastids isolated from irradiated cotyledons just before incubation. They were similar in structure to etioplasts observed in cotyledonary tissue, even to the presence of two-compartmented grana in the peripheral lamellae. No change was induced during isolation whether or not the cofactors were present. However, invaginations from the inner component of the plastid envelope were not distinct in the isolated etioplasts.

Unfortified plastids incubated in the light for 16 hours in the absence of cofactors underwent considerable disorganization (FIG. 4C). In a representative sample of 25 profiles all the plastids were highly degraded. Some degraded etioplasts still possessed an outer envelope or part of one. A much contracted, highly electron-dense prolamellar body was present, embedded in vesicular stroma. Peripheral lamellae were entirely lacking. The vesicular nature of the stroma was difficult to interpret. The individual vesicles appeared to be membrane-bound, and they lacked association with the prolamellar body.

Greening fortified plastids incubated for 16 hours in the light with the cofactors retained much of their normal structure (FIG. 4E). In a representative sample of 28 profiles, 13 exhibited well preserved structures. The intact outer envelope, reacted prolamellar body with peripheral lamellae, and grana are easily identified. One of the peripheral lamellae is associated with the envelope (FIG. 4E). Invagination of the inner component of the envelope was not observed.

Simple overlaps in the membranes of the peripheral lamellae usually occur at this stage of development, and they do appear in the peripheral lamellae of the etioplasts in situ and of the etioplasts isolated both with and without cofactors. Grana formation is usually confined to short (0.5–1 $\mu$ lengths of the peripheral lamellae (FIGS. 4A, 4B, 4D). However, during incubation in the presence of the cofactors, grana appear to form over much of the length of the peripheral lamellae in most of the preserved plastids (FIG. 4E).

Figure 5:
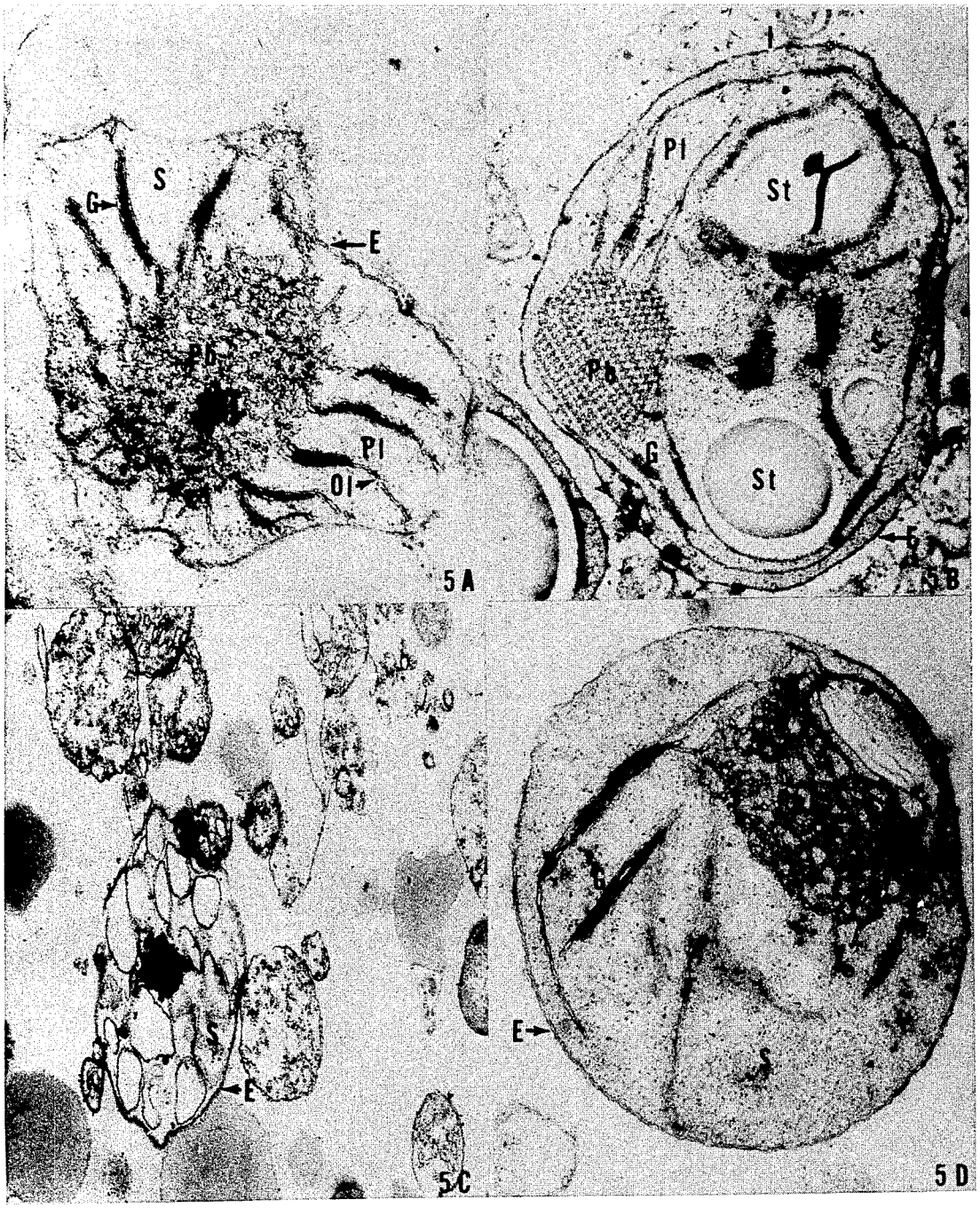
FIG. 5 is a composite comparative photomicrograph of developing chloroplasts.

3. Ultrastructural Changes of Developing Chloroplasts Prepared from 4.5-hour-irradiated Cotyledons, Incubated in the Light in the Absence and Presence of Cofactors FIG. 5 is a composite photomicrograph illustrating ultrastructural changes in developing chloroplasts obtained according to the invention through irradiation for 4.5 hours. The same abbreviations are employed in FIG. 5 as were employed in FIG. 4. FIG. 5A shows an in situ plastid from an irradiated cotyledon; FIG. 5B shows an in situ plastid from irradiated cotyledons incubated at low light for 16 hours; FIG. 5C shows unfortified plastids after 16 hours of incubation without cofactors; and FIG. 5D shows a fortified plastid after 16 hours of incubation with cofactors. All micrographs are at a magnification of 18,000 ×, except for FIG. 5C which has a magnification of 9,000 ×.

Greening cucumber cotyledons irradiated for 4.5 hours with 240 foot-candles of white fluorescent light contained plastids with reacted prolamellar bodies and two- to four-compartment grana arranged along the numerous radiated peripheral lamellae (FIG. 5A). In a representative sample of 23 profiles the plastids were very similar to the one shown in FIG. 5A. The outer ends of several of the peripheral lamellae were closely associated with the outer envelope, giving the usual impression of reaction between envelope and peripheral lamella (FIG. 5A). Such cotyledons had emerged from the lag phase.

When the irradiated cotyledons were moistened with distilled water and exposed to 10 foot-candles of white fluorescent light for 16 hours, the prolamellar bodies reverted to the crystalline condition and some two- and four-compartment grana grew into six-compartment grana (FIG. 5B).

When unfortified developing chloroplasts were isolated from 4.5-hour-irradiated cotyledons and incubated for 16 hours in subdued light in the absence of the cofactors, extensive degradation of the chloroplast structure occurred (FIG. 5C). In a representative sample of 60 profiles all the plastids were highly degraded. The outer envelope was broken. The tubular structure in the prolamellar body was largely obliterated, and it remained as a very electron-dense body, indicating disintegration. No peripheral lamellae were present. The stroma was vesicular, and although the vesicle appeared to be membrane-bound, no evidence of their origin was apparent.

When fortified developing chloroplasts were isolated and incubated for 16 hours in subdued light in the presence of the cofactors, the structure of some of the plastids was remarkably well preserved (FIG. 5D). In a representative sample of 29 profiles, 12 exhibited well maintained structures. The reacted prolamellar body did not revert to the crystalline condition, as was the case with the chloroplasts incubated in situ (FIG. 5B). The grana formed on the peripheral lamellae by the end of the incubation period were unusually long. Some had as many as 10 compartments. The end of one of the peripheral lamellae was closely associated with the plastid envelope, indicating reaction between the envelope and the peripheral lamellae.

C. Summary

Incubation of fortified and unfortified crude homogenates with and without the addition of the cofactors resulted in the breakdown of the etioplasts. The process of degradation was somewhat retarded in the presence of the cofactor mixture.

When unfortified etioplasts were incubated in the dark without the cofactors, the prolamellar body underwent complete disintegration. On the other hand, when fortified etioplasts were incubated in the presence of these cofactors, the prolamellar body was maintained, but it changed from the crystalline to the reacted state.

Developing chloroplasts isolated from cotyledons after 2.5 hours of irradiation and incubated for 16 hours in subdued light showed: (a) without cofactors: an electron-dense disorganized prolamellar body, no peripheral lamellae, and a vesicular stroma (FIG. 4C); (b) with cofactors: a typical, but diffuse reacted prolamellar body, with peripheral lamellae bearing elongated grana and showing some terminal association with the plastid envelope; invagination of the inner component of the envelope was not noted (FIG. 4E).

Whole cotyledons irradiated 4.5 hours and incubated in distilled water in weak light showed a reversion of the reacted prolamellar body to the crystalline state, a typical stroma, and some evidence of the invagination of the inner component of the plastid envelope (FIG. 5B).

Developing chloroplasts isolated from cotyledons after 4.5 hours of irradiation and incubated for 16 hours in the light showed: (a) without cofactors: an electron-dense disorganized prolamellar body, no peripheral lamellae, a vesicular stroma, and a broken outer envelope (FIG. 5C); (b) with cofactors: a typical reacted prolamellar body, with peripheral lamellae bearing somewhat elongated grana. Some had as many as 10 compartments. The ends of some peripheral lamellae were associated with the envelope. The stroma was normal (FIG. 5D).

The in vitro net biosynthesis of chlorophyll according to the present invention may be illustrated by the following exemplary procedures, generally designated as "Procedure II."

PROCEDURE II

A. Materials and Methods

1. Germinating Cumcumber Seeds

Cumcumber seeds (*Cucumis savitus* L. cv. Alpha Green) were germinated in vermiculite at 24°C. in complete darkness for 4 days.

2. Light Pretreatment of Etiolated Cumcumber Cotyledons

Etiolated cotyledons were harvested with full hypocotyl hook under a green safelight as described supa. They were placed in culture dishes with enough distilled water to keep them moist. The excised cotyledons were illuminated with 240 foot-candles of white fluorescent light at 28°C. for 1 minute or for 1, 2, and 4.5 hours. Other light pretreatments were aimed at removing the lag phase by a short pre-illumination followed by dark incubation. (See, Hardy, et al., Plant Physiol., 47, 705-08 (1971).) This was achieved by irradiating the excised cotyledons for 4 minutes with 250 foot-candles of white fluorescent light. The irradiated cotyledons were returned to darkness for 3 hours at 28°C., then illuminated for 4 minutes to phototransform the protochlorophyll (the mixture of protochlorophyllide and protochlorophyllide phyryl ester which accumulates in etiolated tissues) formed during the dark incubation.

3. Isolation of Greening Etioplasts

"Fortified" and "unfortified" plastid preparations refer to isolated greening etioplasts or developing chloroplasts prepared with or without cofactors (GSH, CoA, methyl alcohol, magnesium, Pi, NAD, ATP, and potassium) in the homogenization buffer. Unfortified plastids were prepared by removing the hooks and grinding gently 5 g. of greening cotyledons with mortar and pestle without sand. The grinding was accomplished in 7.5 ml. of 0.5 M sucrose, 0.2 M tris-HCl, pH 8.0, at 0° to 50°C. The brei was filtered through four layers of cheesecloth, and the resulting homogenate was centrifuged at 0°C. for 3 minutes at 200 × g. The supernatant was centrifuged for 7 minutes at 1,500 ×g, and the plastid pellet was suspended in 0.5 M sucrose, 0.2 M tris-HCl, pH 7.7. Fortified plastids were prepared by grinding 5 g. of greening cotyledons in 7.5 ml. of fortified 0.2 M tris-HCl, 0.5 M sucrose, pH 8.0, containing 37.5 $\mu$moles of GSH, 2.25 $\mu$moles of CoA, 3.75 $\mu$moles of magnesium chloride, 375 $\mu$moles of potassium phosphate, 180 $\mu$moles of methyl alcohol, 3 $\mu$moles of ATP, and 0.56 $\mu$mole of NAD. The plastids were sedimented as described above, and the pellet was suspended in the fortified trissucrose buffer at pH 7.7. The plastids extractable from 5 g. of cotyledon were generally used for a single assay. This represented 4 to 7 mg. of proteins per assay. Total proteins were determined by biuret as described in Rebeiz, et al., *Plant Physiol.*, 40, 281-85 (1965).

4. Incubation of Isolated Plastids and Excised Cotyledons

Two ml. of fortified and unfortified plastid suspensions were incubated in cylindrical flat bottom glass tubes (2 × 10 cm.) on a metabolic shaker operated at about 10 to 50 shakes per minute (preferably 10). The incubations were performed at 28°C. under 10 foot-candles of white fluorescent light for 1 hour. Two and a half ml. of unfortified reaction mixture at pH 7.7 contained 400 $\mu$moles of tris-HCl, 1 mmole of sucrose, and 1 $\mu$mole of ALA. The fortified reaction mixture of 2.5 ml. at pH 7.7 contained, in addition to the above components, 100 $\mu$moles of potassium phosphate, 1 $\mu$mole of magnesium chloride, 10 $\mu$moles of GSH, 0.6 $\mu$mole of CoA, 1.2 mmole of methyl alcohol, 0.8 $\mu$mole of ATP, and 0.15 $\mu$mole of NAD.

For reference purposes 10 pairs of preirradiated cotyledons excised with full hypocotyl hook were simultaneously incubated in a minimum volume of distilled water at 28°C. under 250 foot-candles of white fluorescent light. Ten pairs of preirradiated cotyledons served as a zero hour control.

5. Separation of the Products of Incubation

At the beginning or end of incubation, the 2.5-ml. reaction mixtures were transferred to 50-ml. centrifuge tubes with an eye dropper. The reaction was stopped by the addition of 10 ml. of acetone. The incubation vessels were washed free of pigments with 6 to 8 drops of 80% aqueous acetone (v/v) followed by 3 drops of water. The washes were added to the centrifuge tube. After centrifugation at 39,000 × g for 10 minutes, the 80% acetone extracts were decanted and adjusted to a known volume. If the 80% acetone extracts were slightly turbid, te turbidity was eliminated by the addition of 2 to 5 drops of water. The 80% acetone extracts were used for the spectrophotometric determination of extractable chlorophyll and photochlorophyll. It was also used for recording absorption and difference spectra. The green pellets were uniformly suspended in 12 or 24 ml. of 0.2 M tris-HCl, 0.5 M sucrose, pH 8.0, for spectrofluorometric determination of precipitated chlorophyll.

6. Extraction of Excised Incubated Cotyledons

Ten preirradiated cotyledon pairs incubated in water were homogenized for 3 minutes at 0°C. in 10 ml. of acetone-0.1 N ammonium hydroxide (9:1 v/v). The homogenate was centrifuged at 39,000 × g for 10 minutes. The supernatant was decanted, and the pellet was washed with a few ml. of 80% aqueous acetone (v/v). The acetone extract and wash were combined for spectrophotometric determinations. The pellet was suspended in 10 ml. of water, and aliquots were used for the determination of the total cotyledonary proteins.

7. Spectrophotometric Determinations.

Matched cells of 1 cm. internal length and a spectrophotometer were used for the determination of chlorophyll and protochlorophyll in the 80% acetone extract. All absorbancies were corrected for slight light scattering by referring to wavelength-dependent scatter calibration curves. Absorption and difference spectra were recorded with a double beam spectrophotometer. The amounts of extrable chlorophyll *a*, chlorophyll *b*, and protochlorophyll were determined according to Anderson et al., *Aust. J. Biol. Sci.*, 17, 93–101 (1964).

8. Spectrofluorometric Determinations

The chlorophyll that precipitated with the proteins when fortified reaction mixtures were stopped by the addition of acetone was not extractable in organic solvents; it was estimated spectrofluorometrically.

Spectrofluorometric determinations were made with a spectrophotometer supplied with a fluorescence attachment. The latter accommodated an ultraviolet filter. The exciting light had a maximum emission at about 350 nm and a half intensity band width of about 40 nm. The instrument settings for all determinations were as follows: slit 0.9 mm, sensitivity 300, photomultiplier 20 ×, and time constant 0.1. The green pellet was suspended in a total volume of 12 or 24 ml. of 0.2 M tris-HCl, 0.5 M sucrose, pH 8.0. All pellets of the same experiment were adjusted to the same volume. The apparent emission between 750 and 550 nm was recorded on a 3-ml. aliquot. The same tube was used for all samples of the same experiment. The spectral region between 750 and 550 nm was scanned in about 1.1 minutes at 2° to 5°C. Before every recording, the response of the apparatus was checked by measuring the fluorescence output from a red filter, with an apparent emission maximum at 690 nm. Corrections in sensitivity were made accordingly. However, the stability of the light source was fairly high and corrections were infrequently made during an experiment. The apparent emission spectra thus obtained were not corrected for the wavelength-dependent photomultiplier sensitivity or monochromator efficiency. Since the quantitative data is represented as a difference between two identical samples which were scanned through the same wavelength region before and after incubation, the correction is essentially a constant. It does not, therefore, interfere with the quantitation of the apparent differences in fluorescence intensity. The relative fluorescence intensity at the apparent emission maximum was converted to nanomoles of chlorophyll by referring to a standard curve. The curve was calibrated in nanomoles of chlorophyll $a + b$ per 3 ml. of tris-sucrose suspension. The construction of the calibration curve is described below.

9. Preparation of the Standard Chlorophyll Fluorescence Curve.

Etiolated cotyledons were harvested with full hypocotyl hooks and irradiated for 24 hours as described above. The cotyledons were homogenized in 0.2 M tris-HCl, 0.5 M sucrose, pH 8.0, and the unfortified plastids were prepared as already described. They were suspended in 0.2 M tris-HCl, 0.5 M sucrose, pH 7.7. Aliquots in duplicate were brought to a total volume of 4.0 ml. with the unfortified suspension buffer at pH 7.7. One ml. of water was added, and the proteins were precipitated with 20 ml. of acetone. After centrifugation at 39,000 × g for 10 minutes, the supernatant was decanted. One of the two identical green pellets was suspended in 3 ml. of 0.2 M tris-HCl, 0.5 M sucrose, pH 8.0, and its apparent emission spectrum recorded as already described. The duplicate green pellet was extracted with 4 ml. of 80% acetone. After centrifugation the amount of chlorophyll $a$ and $b$ in the 80% acetone extract were determined as already described. In the absence of cofactors, the second 80% acetone extraction freed the pellet from nearly all the chlorophyll pigments. The amounts of chlorophyll $a + b$ were plotted against the corresponding relative emission intensity at the apparent fluorescence maximum. Within the concentration range used, the fluorescence of 3 ml. aliquots of the bound chlorophyll fractions suspended on tris-sucrose varied linearly with the amount of chlorophyll determined spectrophotometrically (FIG. 1).

10. Preparatioan of Pigment Standards

Chlorophyll $a + b$ was prepared from greening cucumber cotyledons and purified by thin layer chromatography. A sub-chloroplastic soluble enzyme system ($S_3$) capable of uro, copro, and protoporphyrin biosynthesis and accumulation was prepared from developing chloroplasts. It was incubated with 25 $\mu$moles of ALA and cofactors for 16 hours.

B. Results

1. Biosynthetic Activity of Developing Chloroplasts Prepared from 4.5-hour-Preirradiated Cotyledons and Incubated with Cofactors for 1 Hour.

FIG. 2A shows absorption spectra of the 80% acetone extract of fortified developing chloroplasts prepared from 4.5-hour-preirradiated cotyledons. In FIG. 2A, (—) indicates values before incubation and (- - -) indicates values after 2-hour incubation. FIG. 2B shows difference spectra for the same type of materials. In FIG. 2B, (—●—) indicates the values of the difference spectrum (2 hours - 0 hours): (—O—) the values of the difference spectrum (1 hour - 0 hours) after 1 hour of incubation. "CHl" indicates absorbance due to chlorophyll $a + b$, and "Ca" the absorbance due to carotinoids. Arrows indicate absorption due to porphyrins. Breaks in spectra indicate a shift to a less expanded ordinate scale.

Figure 2:
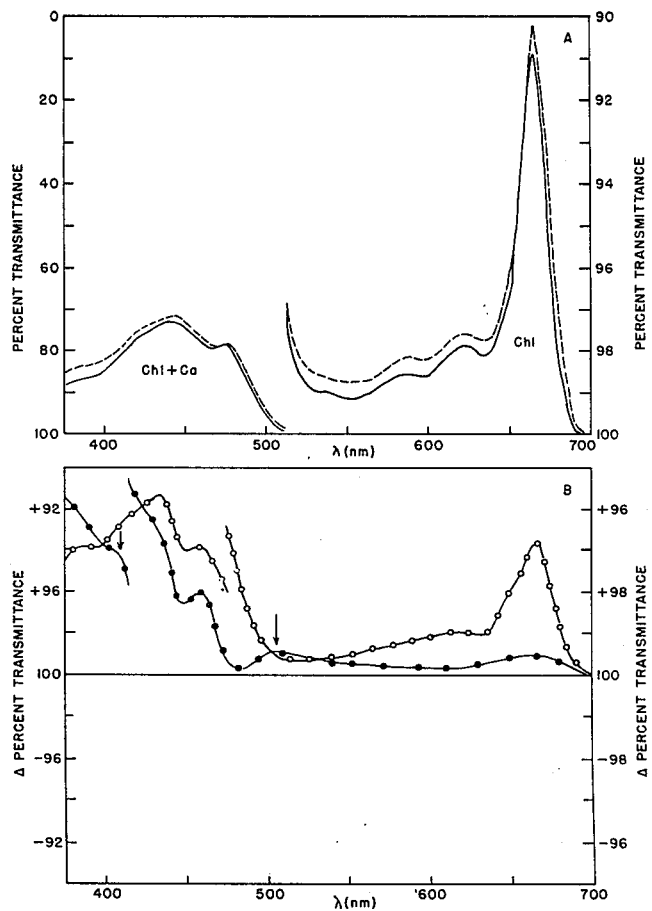

Extraction of the fortified reaction mixtures before and after 1 hour of incubation yielded a yellow-green 80% acetone extract and a green pellet. Chlorophyll in the acetone extract is referred to as "extractable chlorophyll." Chlorophyll in the green pellet is referred to as "bound chlorophyll." Pellets precipitated with acetone from unfortified and fortified reaction mixtures are referred to as unfortified and fortified pellets respectively. The absorption spectra of the 80% acetone extracts obtained before and after 1 hour of incubation with cofactors were qualitatively identical. There was no evidence of prophyrin accumulation (FIG. 2). Chromatographic analysis failed to detect chlorophyll and carotenoid degradation. However, after 2 hours of incubation with cofactors minor amounts of porphyrins started to accumulate (FIG. 2). This was evidenced in the difference spectrum "2 hours - 0 hours" by the appearance of the fourth absorption band of free porphyrins around 500 nm and a Soret band around 400 nm (FIG. 2B).

Unfortified pellets contained less chlorophyll than fortified one (Table III, infra). They were thoroughly re-extractable with 80% acetone before and after incubation; only trace amounts of chlorophyll remained in the unfortified pellet after a second acetone extraction (FIG. 3).

All attempts failed to re-extract the bound chlorophyll of the fortified pellets with 80% acetone, methanol, ethanol, ether, hexane, ethanol:ether (1:1 v/v), strong acids, or bases. The green pellet was sticky and difficult to manipulate. It was easily suspended in 0.2 M tris-HCl, 0.5 M sucrose, pH 8.0 The suspension was homogeneous and lent itself to the spectrofluorometric determination of bound chlorophyll. Formation of bound chlorophyll depended on the continous presence of cofactors in the fortified crude homogenate and in the reaction mixture prior to addition of acetone. A bound chlorophyll fraction was obtained from fortified reaction mixtures before and after incubation (Table I, infra).

Figure 3:
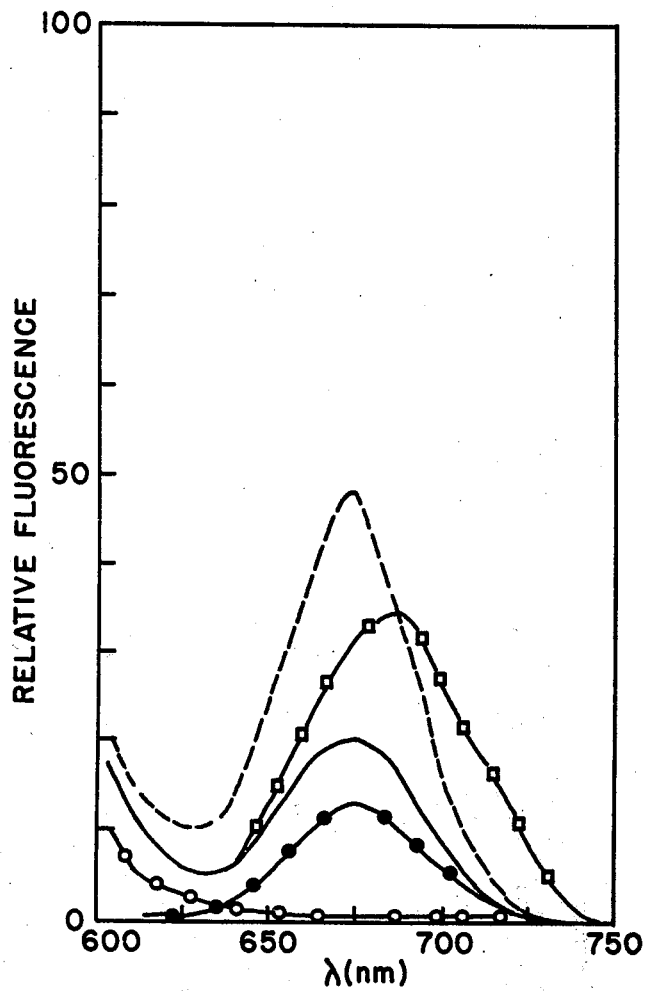

FIG. 3 shows apparent fluorescence spectra of various bound chlorophyll fracton derived from fortified developing chloroplasts, prepared from 4.5-hour irradiated cotyledons as follows: at 0 hour before precipitation with acetone ( □ ); standard chlorophyll $a + b$ (3:1) in 80% acetone (—●—); bound chlorophyll fraction precipitated from a fortified reaction mixture before incubation (—); bound chlorophyll fraction from the same reaction mixture after 1 hour of incubation ( – – – ); unfortified pellet precipitated from an unfortified reaction mixture at 0 hour, after a second acetone extraction (—O—). The bound chlorophyll fractions were suspended in equal volumes of 0.2 M tris-HCl, 0.5 M sucrose, pH 8.0; the spectra were recorded on 3-ml. aliquots.

Figure 6:
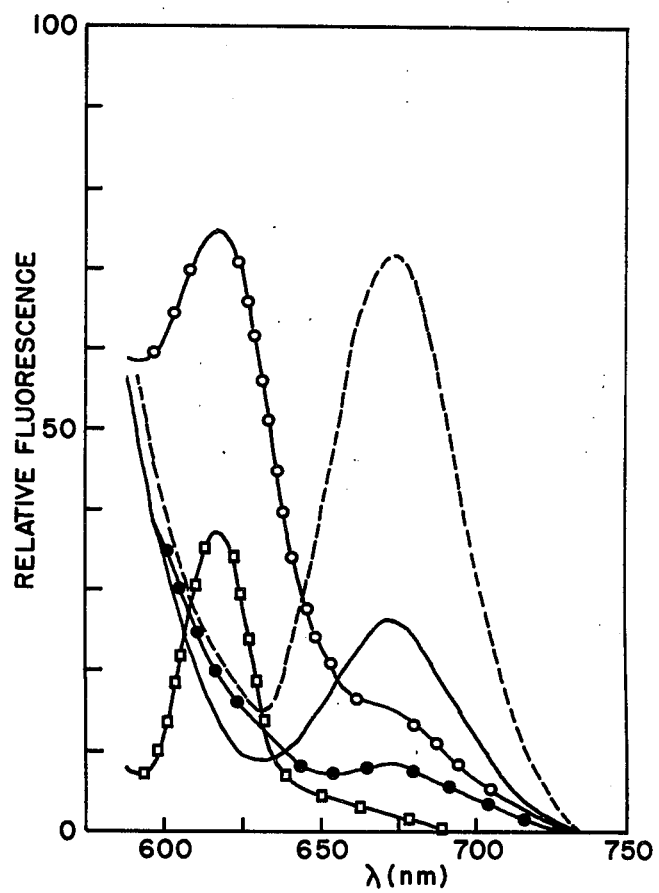
FIG. 6 graphically represents apparent fluorescence of bound chlorophyll fractions.

FIG. 6 shows apparent fluorescence spectra of bound chlorophyll fractions before and after 1 hour of incubation, in the absence and presence of cofactors, of fortified and unfortified developing chloroplasts prepared from 4.5-hour irradiated cotyledons, as follows: without cofactors, 0 hour (—●—); without cofactors, after 1 hour of incubation (—O—); with cofactors, 0 hour (—); with cofactors, after 1 hour of incubation ( – – – ); pellet precipitated from a standard fortified $S_3$ incubation mixture that accumulated uro, copro, and protoporphyrin ( □ ). The spectrum of the $S_3$ standard was determined on a small aliquot adjusted to 3 ml. with tris-sucrose.

The apparent emission spectrum of bound chlorophyll in tris-sucrose was similar to that of a 3 to 1 mixture of chlorophyll $a + b$ dissolved in 80% acetone (FIG. 3). It exhibited an apparent emission peal at 673 to 676 nm. This corresponded to a blue shift of about 12 nm with respect to the emission maximum of fortified developing chloroplasts (FIG. 3). No evidence of porphrin emission at 617 to 619 nm was detected after 1 hour of incubation (FIGS. 3 and 6). Increases in chlorophyll and protochlorophyll content of 42 and 32%, respectively, occurred after 1 hour of incubation (Table I, infra). In this particular experiment, the increase in chlorophyll was confined to bound chlorophyll. The apparent emission of the bound chlorophyll is depicted in FIG. 3. For reference purposes, the chlorophyll accumulation in situ of excised greening cotyledons incubated under 240 foot-candles of white fluorescent light is also shown (Table I, infra).

Changes in extractable chlorophyll, bound chlorophyll, and protochlorophyll after 1 hour of incubation were monitored in 38 consecutive experiments. Twenty-five experiments exhibited chlorophyll increases, ten showed losses, and three exhibited no change (Table II, infra). Synthesized chlorophyll was either confined to the extractable fraction, to the bound fraction, or to both, but most frequently it was bound. Eleven experiments exhibited protochlorophyll decreases, three indicated no change, and 24 showed increases after 1 hour of incubation (Table II, infra). Changes in protochlorophyll did not necessarily parallel changes in chlorophyll content.

TABLE I

Biosynthetic Activity of Fortified Developing Chloroplasts and Excised Cotyledons Fortified developing chloroplasts were prepared from greening cotyledons preirradiated for 4.5 hour. The fortified reaction mixture was incubated for 1 hour at 28°C. under 10 foot-candle of white fluorescent light. The excised preirradiated cotyledons were incubated in water under 250 foot-candle of the same light.

| Experiment | Pigment | Amount Before incubation | Amount After incubation | Change After Incubation |
|---|---|---|---|---|
| | | nmoles/100 mg. protein | | Δ% |
| Fortified reaction mixture | Protochl. | 22.8 | 30.1 | +32.0 |
| | Extractable chl. | 255.8 | 250.0 | −2.3 |
| | Bound chl. | 123.7 | 290.3 | +134.7 |
| | Total chl. | 379.5 | 540.3 | +42.4 |
| | | nmoles/100 mg. cotyledonary proteins | | |
| Excised cotyledons | Total chl. | 111.8 | 144.8 | +29.5 |

Table II

Survey of 38 Consecutive Experiments Monitoring the Change in Total Chlorophyll and Protochlorophyll of Fortified Developing Chloroplasts

| | \-44 to −20 | −19 to −10 | −9 to −1 | 0.0 | +1 to +9 | +10 to +9 | +20 to +44 | >44 |
|---|---|---|---|---|---|---|---|---|
| | \multicolumn{8}{c}{Change in Pigments after 1 Hour of Incubation Δ%} | | | | | | | |
| | | | | No. of experiments | | | | |
| Total Chl.[1] | | 1 | 9 | 3 | 7 | 12 | 6 | |
| Protochl. | 3 | 3 | 5 | 3 | 5 | 4 | 6 | 9 |

[1]Extractable chlorophyll + bound chlorophyll.

TABLE III

Biosynthetic Activity of Unfortified and Fortified Developing Chloroplasts

The developing chloroplasts were prepared from greening cotyledons preirradiated for 4.5 hour.

| | Pigment | Amount Before incubation | Amount After 1 hour of incubation | Change After Incubation |
|---|---|---|---|---|
| | | nmoles/100 mg. proteins | | Δ% |
| Experiment A − Cofactors | Porphydrins[1] | none | + | |
| | Protochl. | 22.4 | | |
| | Extractable chl. | 236.4 | 227.1 | |
| | Bound chl. | 10.8 | 3.3 | |
| | Total chl. | 247.2 | 230.4 | −6.8 |
| + Cofactors | Porphydrins[1] | none | none | |
| | Protochl. | 18.0 | 21.3 | |
| | Extractable chl. | 200.0 | 169.2 | |
| | Bound chl. | 134.2 | 259.3 | |
| | Total chl. | 334.2 | 428.5 | +28.2 |
| Experiment B − Cofactors | Porphyrins[1] | none | + | |
| | Protochl. | trace | | |

-continued

| Pigment | | Amount Before incubation | After 1 hour of incubation | Change After Incubation |
|---|---|---|---|---|
| + Cofactors | Extractable chl. | 402.0 | 402.3 | |
| | Bound chl. | 22.9 | 10.3 | |
| | Total chl. | 424.9 | 412.6 | −2.9 |
| | Porphyrins[1] | none | none | |
| | Protochl. | 19.7 | 18.0 | |
| | Extractable chl. | 180.1 | 180.1 | |
| | Bound chl. | 51.6 | 134.2 | |
| | Total chl. | 231.7 | 314.3 | +35.6 |

[1]The plus sign denotes prophyrin accumulation.

2. Biosynthetic Activity of Unfortified Developing Chloroplasts Prepared from 4.5-hour-Preirradiated Cotyledons and Incubated without Cofactors for 1 Hour After 1 hour of incubation in the absence of cofactors, extractable chlorophyll decreased or remained unchanged (Table III). The bound chlorophyll fraction exhibited a strong apparent emission at 617 to 619 nm (FIG. 6). The net chlorophyll emission at 673 to 676 nm decreased; it appeared as a weak shoulder on the long wavelength tail of the 617 to 619 nm band (FIG. 6, Table III), The apparent emission at 617 to 619 nm was identical to the apparent emission of a fortified acetone pellet precipitated from a standard fortified $S_3$ incubation containing uro, copro, and protoporphyrin (FIG. 6). It was not possible to determine the amount of protochlorophyll formed after 1 hour of incubation, in the presence of unknown quantities of porphyrins, since the simultaneous equations used here did not correct for porphyrin absorption at 620 to 630 nm.

After 1 hour of incubation in the presence of coofactors, no porphyrin emission was detected in the bound chlorophyll fraction. Instead it exhibited a substantial increase in chlorophyll content (FIG. 6, Table III). The extractable chlorophyll either decreased or remained unchanged. Protochlorophyll either decreased or accumulated slightly (Table III).

Various experiments were designed to test whether trace amounts of added porphyrins would enhance the fluorescence yield of bound chlorophyll. They failed to show any net increase in chlorophyll emission.

These results indicated that after 1 hour of incubation in the absence of cofactors total chlorophyll descreased slightly and porphyrins accumulated. The presence of cofactors prevented the accumulation of free porphyrins and enhanced the accumulation of chlorophyll (FIG. 6, Table III).

TABLE IV

Biosynthetic Activity of Greening Etioplasts Extracted from Etiolated Cotyledons Cotyledons were submitted to various light-dark regimes at 250 foot-candle of white fluorescent light and 28°C.

| Experiment | Light-Dark Regime | Pigment | Amount Before incubation | After incubation | Change After Incubation | $\Delta$[1] protochlorophyll/$\Delta$ chlorophyll |
|---|---|---|---|---|---|---|
| | | | nmoles/100 mg. protein | | $\Delta$% | |
| A | 1 min. light | Protochl. | 15.9 | 44.0 | +177 | |
| | | Extractable chl. | 25.5 | 40.4 | | 1.3 |
| | | Bound chl. | 0.0 | 7.3 | | |
| | | Total chl. | 25.5 | 47.7 | +87 | |
| B | 1 hr. light | Protochl. | 8.3 | 26.3 | +217 | |
| | | Extractable chl. | 21.3 | 26.6 | | 2.6 |
| | | Bound chl. | 3.2 | 4.8 | | |
| | | Total chl. | 24.5 | 31.4 | +28 | |
| C | 2 hr. light | Protochl. | 11.1 | 40.0 | +260 | |
| | | Extractable chl. | 44.3 | 72.5 | | 1.2 |
| | | Bound chl. | 15.1 | 10.4 | | |
| | | Total chl. | 59.4 | 82.9 | '40 | |
| D | 4.5 hr. light | Protochl. | 21.0 | 23.1 | +10 | |
| | | Extractable chl. | 165.6 | 189.9 | | 0.04 |
| | | Bound chl. | 28.2 | 59.6 | | |
| | | Total chl. | 193.8 | 249.5 | +29 | |
| E | 5 min. light + 3 hr. dark + 5 min. light | Protochl. | 2.6 | 31.1 | +1096 | |
| | | Extractable chl. | 17.3 | 28.3 | | 2.1 |
| | | Bound chl. | 4.1 | 6.8 | | |
| | | Total chl. | 21.4 | 25.1 | +64 | |

[1]Refers to the ratio of the increment in pigment after 1 hour of incubation.

3. Biosynthetic Activity of Developing Chloroplasts Extracted from Etiolated Cotyledons Submitted to Short Light Pretreatments The biosynthetic activity of greening etioplasts that were in the lag phase is presented in Table IV. The amount of bound chlorophyll detected at 0 hour depended on the length of preirradiation and little had accumulated at the end of incubation. Most of the increase in chlorophyll was confined to extractable chlorophyll. This was in contrast to developing chloroplasts obtained from rapidly greening cotyledons preirradiated for 4.5 hours (Table IV).

Etioplasts that were in the lag phase showed higher rates of nonphototransformable protochlorophyll biosynthesis than chlorophyll. This was illustrated by a high ratio of newly synthesized nonphototransformable protochlorophyll (which may contain some protoporphyrin IX) to chlorophyll in lag phase etioplasts after 1 hour of incubation. This ratio was very low in developing chloroplasts extracted from rapidly greening cotyledons that were preirradiated for 4.5 hours (Table IV).

In order to determine whether the above biosynthetic pattern was lag phase dependent or not, the lag phase was artificially removed by a short light pretreatment followed by a dark incubation. Such treatment removes the lag phase of chlorophyll biosynthesis without the need of continuous irradiation. Removal of the lag phase under these conditions did not change the biosynthetic pattern (Table IV). The bound chlorophyll fraction remained minimal. Most of the newly synthesized chlorophyll was confined to the extractable fraction. The plastids exhibited a typical high ratio of nonphototransformable protochlorophyll to chlorophyll biosynthesis (Table IV).

Upon consideration of Preparations I and II, above, it is apparent that there exist preferred ranges of process parameters, within the broad ranges earlier stated, for performing the processes of the present invention. Thus, for example, the irradiation step is preferably performed in the presence of air, with visible light of an intensity in the vicinity of 250 foot-candles, for a duration of about 4 hours, and at a temperature in the vicinity of 28°C. Similarly, the homgenization step is preferably performed at a temperature in the vicinity of about 5°C. and with the buffer having a pH of 8.0, as measured at 20°C. Likewise, the incubation step is preferably performed in the presence of air, with visible light of an intensity of 5–10 foot-candles, at a temperature in the vicinity of 28°C. and with a buffer having a pH of 7.7, as measured at 20°C. The shaking rate of the incubation step is preferably 10 shakes/minute. Further, it is preferable to incorporate the magnesium into the buffers as magnesium chloride and to incorporate the potassium and Pi concurrently as potassium phosphate. It should be clear to those skilled in the art that performance of the various processes at the extremes of parameter ranges earlier stated may yield less than optimal results.

It is expected that the processes of the present invention may be performed in a potentially enhanced manner through inclusion of one or more of the following cofactor materials in the homogenization and incubation buffer media: vitamin E; ascorbic acid; NAD phosphate; ammonium chloride; phosphocreatin; guanosin triphosphate; phenylalanine; leucine; valine; glycine; alanine; methionine; hydroxy proline; arginine; histidine; serine; cysteine; glutamic acid; isoleucine; lysine; threonine; glutamine; proline; asparagine; aspartic acid; cystine; tryptophan; tyrosine; malonic acid; choline chloride; glycerol; D-galactose; D-glucose; potassium bicarbonate; reduced NAD phosphate; reduced NAD; biotin; cytosine diphosphate; uridine triphosphate; acetic acid; potassium sulfate; folic acid; pyridoxyl phosphate; kinetin; sodium pyrophosphate; thiamin pyrophosphate; calcium chloride; giberellic acid; mevalonic acid; indole acetic acid; lipoic acid; phytol; vitamin K; and gluteraldehyde.

Obviously numerous modifications and variations of the invention will occur to those skilled in the art and thus only such limitations as appear in the amended claims should be placed thereon.

What is claimed is:

1. A process for in vitro net biosynthesis of chlorophyll and grana, said process comprising the following steps in relative sequence:

a. irradiating etiolated plant tissue with visible light to precipitate formation of developing chloroplasts in said etiolated tissue;

b. homogenizing said tissue in an environment having available oxygen and in a buffer comprising biosynthetic cofactors including, coenzyme A, glutathione, potassium, inoganic phosphate, methyl alcohol, magnesium, nicotinamide adenine dinucleotide and adenosine triphosphate, which buffer has a pH of from 7.9 to 8.2, as measured at ambient temperature;

c. isolating developing chloroplasts from the homogenate of step (b); and d. incubating, while irradiating with visible light, said developing chloroplasts in an environment having available oxygen and in a buffer comprising biosynthetic cofactors including, δ-aminolevulinic acid, coenzyme A, glutathione, potassium, inorganic phosphate, methyl alcohol, magnesium nicotinamide adenine dinucleotide and adenosine triphosphate, which buffer has a pH of from 7.6 to 7.8, as measured at ambient temperture, to produce chlorophyll and grana.

2. The process of claim 1 further including the step of isolating chlorophyll and grana from the buffer subsequent to step (d).

3. The process according to claim 1 wherein step (a) includes irradiating said tissue with light of an intensity of from about 100 to about 300 foot-candles, for duration of from about 2 to about 5 hours, and at a temperature of from about 20° to about 35°C.

4. The process according to claim 3 wherein the intensity of light is in the vicinity of about 250 foot-candles.

5. The process according to claim 3 wherein the duration is about 4 hours.

6. The process according to claim 3 wherein the temperature is in the vicinity of about 28°C.

7. The process according to claim 1 wherein step (b) includes homogenizing at a temperature in the vicinity of about 5°C.

8. The process according to claim 1 wherein step (d) includes irradiating with visible light of from about 1 to about 50 foot-candles and incubating at a temperature of from about 15°to about 35°C.

9. The process according to claim 8 wherein the intensity of light is in the vicinity of about 5 to 10 foot-candles.

10. The process according to claim 8 wherein the temperature is in the vicinity of about 28°C.

11. The process according to claim 1 wherein step (b) includes homogenizing in a buffer having a pH of 8.0, as measured at 20°C.

12. The process according to claim 1 wherein step (d) includes incubating in a buffer having a pH of 7.7, as measured at 20°C.

13. The process according to claim 1 wherein said etiolated plant tissue is higher plant tissue.

14. The process according to claim 13 wherein said higher plant tissue is cotyledon tissue.

15. The process according to claim 14 wherein said cotyledon tissue is cucumber cotyledon tissue.

16. The process for in vitro net biosynthesis of chlorophyll a, chlorophyll b and grana having chlorophyll a and chlorophyll b associated therewith, said process comprising the following steps in relative sequence:

a. irradiating etiolated plant tissue with visible light of an intensity of from about 100 to about 300 foot-candles, for a duration of from about 2 to about 5 hours, at a temperature of from about 20° to about 35°C., to precipitate formation of developing chloroplasts in said etiolated tissue;

b. homogenizing said tissue in an environment having available oxygen and in a buffer comprising biosynthetic cofactors including, coenzyme A, glutathione, potassium, inorganic phosphate, methyl alcohol, magnesium, nicotinamide adenine dinucleotide and adenosine triphosphate, which buffer has a pH of from 7.9 to 8.2, as measured at ambient temperature;

c. isolating developing chloroplasts from the homogenate of step (b); and d. incubating, while irradiating with visible light of an intensity of from about 1 to about 50 foot-candles, said developing chloroplasts at a temperature of from about 15° to about 35°C., in an environment having available oxygen, and in a buffer comprising biosynthetic cofactors including, δ-aminolevulinic acid, coenzyme A, glutathione, potassium, inorganic phosphate, methyl alcohol, magnesium, nicotinamide adenosine dinucleotide and adenosine triphosphate, which buffer has a pH of from 7.6 to 7.8, as measured at ambient temperature, to produce chlorophyll $a$, chlorophyll $b$ and grana having chlorophyll $a$ and chlorophyll $b$ associated therewith.

17. The process according to claim 16 further including the step of isolating chlorophyll $a$, chlorophyll $b$ and grana having chlorophyll $a$ and chlorophyll $b$ associated therewith from the buffer subsequent to step (d).

* * * * *

UNITED STATES PATENT AND TRADEMARK OFFICE
CERTIFICATE OF CORRECTION

PATENT NO. : 3,934,369
DATED : January 27, 1976
INVENTOR(S) : CONSTANTIN ANIS REBEIZ It is certified that error appears in the above-identified patent and that said Letters Patent are hereby corrected as shown below:

Title stated as Item 54 on cover page should read:
IN VITRO NET BIOSYNTHESIS OF CHLOROPHYLL AND GRANA Col. 1, line 1 - "BIOXYNTHESIS" should be --BIOSYNTHESIS--

Col. 5, line 54 - "adsence" should be --absence--

Col. 9, line 50 - "50°C" should be --5°C--

Col. 13, line 45 - "peal" should be --peak--

Col. 13, line 49 - "porphrin" should be --porphyrin--

Col. 14, line 50 - "preparred" should be --prepared--

Col. 16, line 37 - " '40 " should be -- +40 --

Col. 18, line 22 - "temperture" should be --temperature--

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*